United States Patent [19]

Hinrichsen et al.

[11] Patent Number: 4,950,474

[45] Date of Patent: * Aug. 21, 1990

[54] COMBINATION CORROSION AND SCALE INHIBITING SYSTEM CONTAINING PHOSPHONATE/AMINE REACTION PRODUCT

[75] Inventors: Charles J. Hinrichsen; Frederick W. Valone, both of Houston, Tex.

[73] Assignee: Texaco Inc., White Plains, N.Y.

[*] Notice: The portion of the term of this patent subsequent to Jan. 13, 2004 has been disclaimed.

[21] Appl. No.: 226,332

[22] Filed: Aug. 1, 1988

[51] Int. Cl.$^5$ .................. C23F 11/167; E21B 41/02
[52] U.S. Cl. .................. 422/15; 252/80; 252/8.552; 252/8.555; 252/389.22; 562/12
[58] Field of Search ............ 252/80, 8.552, 389.22, 252/8.555; 422/15; 562/12

[56] References Cited

U.S. PATENT DOCUMENTS

| | | | |
|---|---|---|---|
| 2,996,542 | 8/1961 | Nielsen | 562/12 |
| 3,298,956 | 1/1967 | Irani et al. | 252/389.22 X |
| 3,467,192 | 9/1969 | Nolan et al. | 252/180 X |
| 3,483,925 | 12/1969 | Slyker | 252/80 X |
| 3,619,427 | 11/1971 | Kautsky | 422/15 X |
| 3,770,815 | 11/1973 | Jones | 562/12 |
| 4,636,256 | 1/1987 | Valone | 252/8.555 X |
| 4,846,980 | 7/1989 | Valone | 252/8.552 |

Primary Examiner—Richard D. Lovering
Assistant Examiner—Gary L. Geist
Attorney, Agent, or Firm—Jack H. Park; Kenneth R. Priem; Harold J. Delhommer

[57] ABSTRACT

A series of water-dispersible corrosion and scale inhibiting solutions are disclosed which contain the reaction product of a phosphonate compound containing at least two phosphonate groups of the formula

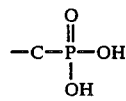

and an ethoxylated, propoxylated alkylphenol amine represented by the formula

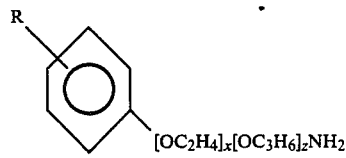

wherein R is an alkyl group containing about 5 to about 12 carbon atoms, X equals about 1 to about 20, and z equals about 1 to about 20.

17 Claims, No Drawings

COMBINATION CORROSION AND SCALE INHIBITING SYSTEM CONTAINING PHOSPHONATE/AMINE REACTION PRODUCT

BACKGROUND OF THE INVENTION

The invention relates to organic inhibitor treating solutions and a method for using such solutions to reduce corrosion and scale from the harsh fluid environments encountered in the oil field. More particularly, the invention concerns treating solutions containing an ethoxylated, propoxylated alkylphenol amine, which are effective in reducing both scale and sweet and sour corrosion.

Corrosion that occurs in an oil field environment is extremely complex and tends to attack all manner of metal equipment above and below ground. The principle corrosive agents found in the well fluids include hydrogen sulfide, carbon dioxide, oxygen, organic acids and solubilized salts. These agents may be present individually or in combination with each other. Valves, fittings, tubing, pumps, pipelines, sucker rods, and other producing equipment are particularly susceptible. Deposiss of rust, scale, corrosion by-products, paraffin and other substances create ideal environments for concentration cells. Carbon dioxide and hydrogen sulfide induced pitting is encouraged by such deposits. Acidic condensate that collects on metal tubing will also cause pitting. Extreme temperatures and pressures in downhole environments further accelerate corrosion.

Very often as oil fields mature and enhanced recovery methods such as water flooding and miscible flooding are instituted, the concentrations of hydrogen sulfide and carbon dioxide in the well fluids increase dramatically. This increase in concentration and the resultant increase in sweet corrosion or sour corrosion may make older oil fields economically unattractive due to excessive corrosion costs.

Various surfactants have been employed for many years to inhibit corrosion or to improve the performance of certain organic corrosion inhibitor systems. Surfactants are generally added to inhibitor systems to perform the different functions of (1) solubilizing the corrosion inhibitor or other active ingredients, (2) clean the surface of the metal to be protected or treated, and (3) improving the penetration of the active ingredients into the microscopic pores of the metal.

Ethoxylated alcohols and ethoxylated amines of various structures are common surfactants employed in corrosion inhibition systems. Four examples of such surfactant compounds are provided by U.S. Pat. Nos. 3,110,683; 3,623,979; 4,435,361 and 4,420,414. U.S. Pat. No. 3,110,683 discloses a series of alkylated, halogenated, sulfonated, diphenyl oxides and U.S. Pat. No. 3,623,979 discloses a series of imidazolinyl polymeric acid amides. The use of dicyclopentadiene sulfonate salts is disclosed in U.S. Pat. No. 4,435,361. Ethoxylated tertiary amines represented by the formula

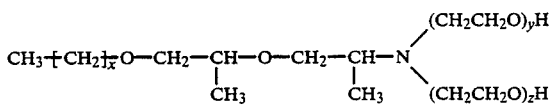

wherein x is about 9-11 and the sum of (y+z) is 2-50 described and claimed in U.S. Pat. No. 4,420,414. All four of the above corrosion inhibition patents disclose oil-dispersible inhibiting systems which form a film over the metal parts to be treated. They are not water soluble systems.

U.S. Pat. No. 4,636,256 discloses a corrosion inhibiting system comprised of the reaction product of a phosphate ester with an alkoxylated amine having the formula

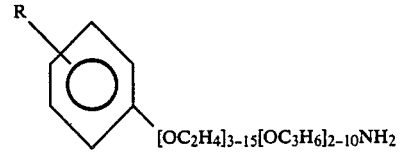

Other alkoxylated amine reaction products are disclosed in U.S. Patent applications Ser. No. 136,064, filed Dec. 21, 1987, now U.S. Pat. No. 4,846,980 and No. 137,646, filed Dec. 24, 1987 now U.S. Pat. No. 4,867,888.

SUMMARY OF THE INVENTION

A series of water soluble, or at least water-dispersible, corrosion and scale inhibiting solutions are disclosed which contain the reaction product of a phosphonate compound containing at least two phosphonate groups of the formula

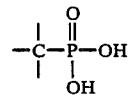

and an ethoxylated, propoxylated alkylphenol amine represented by the formula

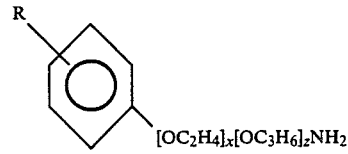

wherein R is an alkyl group containing about 5 to about 12 carbon atoms, x equals about 1 to about 20, and z equals about 1 to about 20. It has been discovered that the use of these particular phosphonate/amine reaction products dramatically reduces oil field scale and corrosion rates.

It is preferred that the phosphonate/amine reaction product be used in a continuous treatment wherein the metal to be protected from corrosion and scale is contacted with about 3 to about 200 ppm of the reaction product in a continuous treatment. The compounds, however, can be stored and shipped in solutions with concentrations ranging up to and greater than 70% phosphonate/amine reaction product by volume. Of course, the instant compounds may also be combined with other organic corrosion and scale inhibiting systems to produce excellent results.

Metal equipment can be protected through the use of the corrosion and scale inhibiting solutions of the present invention by contacting metal with an effective amount of inhibiting solution containing the phosphonate/amine reaction products of the instant formula in a continuous exposure treatment. Solution concentration preferably should be in the range of about 3 ppm to about 200 ppm in a continuous exposure treatment.

DETAILED DESCRIPTION

Perhaps the most costly problem in an oil field environment is corrosion of piping and equipment due to sweet and sour corrosion. It has been discovered that the additions of small amounts of the reaction product of a phosphonate compound having at least two phosphonate groups and an alkoxylated alkylphenol amine effectively inhibits scale and corrosion from both carbon dioxide and hydrogen sulfide.

Although this invention comprises combination scale and corrosion inhibiting solutions containing about 2 ppm to about 70% by volume of the instant reaction product, the compound is preferably delivered to the metal sites in a continuous treating solution containing about 3 ppm to about 200 ppm of the phosphonate/amine reaction product. The amine utilized has the formula

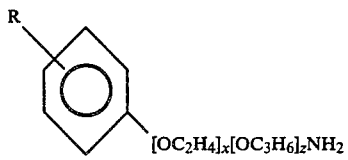

wherein R is an alkyl group containing about 5 to about 12 carbon atoms, x equals about 1 to about 20, and z equals about 1 to about 20. The phosphonate compound has at least two, preferably about two to about six phosphonate groups of the formula

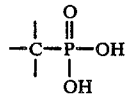

The phosphonate/amine reaction products most preferred for use in the invention combination corrosion and scale inhibiting solutions are those compounds wherein the amine reactant is an alkyl group containing about 7 to about 10 carbon atoms, x equals about 4 to about 11 and z equals about 2 to about 5. The alkyl group containing about 5 to about 12 carbon atoms is necessary to add non-polar material to the compound. The elimination of the alkyl group may make the compound too water soluble. If the R group is absent, it is believed that there would not be enough non-polar material to keep the aqueous phase off the metal. The isomeric positions of the alkyl group and the chain of alkylene oxide groups on the aromatic ring are thought to be unimportant. The structures of the phosphonate and amine may be varied to tailor the reaction product to individual requirements, most particularly, desired solubility.

The amine reactants used to prepare the phosphonate reaction product may be synthesized by the reaction of ethylene and propylene oxide with an alkylphenol in varying ratios. The resulting compound is then subjected to reductive amination in the presence of ammonia and hydrogen to produce the amine reactant.

The effectiveness of a given organic inhibitor system generally increases with the concentration, but because of cost considerations, most solutions when fully diluted in their working environment must be effective in quantities of less than about 0.01% by weight (100 ppm). The invention solution is effective throughout the range of about 3 ppm to about 200 ppm in a continuous injection method, with higher concentrations generally producing greater protection. Although it may not be cost effective, the invention inhibiting solution may be employed in the field with 1% by volume of the phosphonate/amine reaction product.

It is desirable to store and transport the invention corrosion solution with higher reaction product concentrations, such as about 1% to about 70% by volume, preferably about 15% to about 60% by volume of the solution. Depending upon the amine and phosphonate reacted, the reaction product may or may not be soluble in water. But all of the invention compounds are at least highly dispersible in water at the treating concentrations of about 2 ppm to about 1%. When higher concentrations are used for storage and transportation, it may be necessary to add some alcohol to the water solvent to maintain the active ingredient in solution. With only water as a solvent at these higher concentrations, settling problems may occur which would make dilution and use in the field quite difficult. For handling ease and to save volume and shipping costs, concentrations are preferably about 30% to about 80% water, about 5% to about 40% alcohol, and about 15% to about 60% of active ingredient by volume of solution.

In higher concentrations of about 15% to about 60% by volume of the instant reaction product, it is preferred that the solvent contain at least some portion of a lower molecular weight alcohol to maintain solubility, or at least dispersion, of the amine. This avoids physical handling problems in the field. Practically any alcohol may be used as a solvent, but lower molecular weight alcohols are preferred, primarily because of their low cost. Methanol, isopropanol and ethylene glycol are three of the most preferred alcohol solvents.

Methanol is a preferred alcohol solvent because of its cost. Ethanol, propanol, isopropanol, butanol and pentanol may all be used. Ethylene glycol and propylene glycol are also preferred alcohol solvents because they can be mixed with methanol or the other alcohols to lower the flash point and pour point of the solution. Consequently, a representative concentrated solution might be 25% phosphonate/amine reaction product in a 75% solvent of 5% methanol, 15% ethylene glycol and 55% water. Of course, much larger amounts of alcohol may be employed, but water is preferred because of its cost.

The phosphonate compound and amine are preferably reacted in the stoichiometric proportions of about 0.9/1 phosphonate/amine ratio to about 1/0.9 phosphonate/amine ratio. The use of phosphonate or amine in excess of this preferred ratio will yield the desired phosphonate/amine reaction product and excess phosphonate or amine in solution.

The combination corrosion and scale inhibiting solutions of the invention which contain the instant phosphonate/amine reaction products may be employed in different locations in the oil field. These solutions are also effective enough against both corrosion and scale to be used for both purposes at once. Since the solutions offer substantial improvement over present inhibitor systems, they may be used to protect downhole piping and equipment in situations such as subsurface water injection for pressure maintenance, water disposal systems or drilling and production applications, as well as in above-ground, oil or water flow lines and equipment.

The invention solution may be employed to inhibit scale and corrosion by continuous injection. In a continuous injection treatment, the active ingredient of the scale and corrosion inhibiting solution is maintained at the required levels of treatment, most preferably about 5 ppm to about 300 ppm, in areas where corrosive fluids contact the metallic parts desired to be protected.

At present, an industry established procedure for testing oil field scale and corrosion inhibitors does not exist. Because of widely varying corrosion conditions in the oil field, it is impractical to establish a universal standard laboratory test. But it is desirable to have tests that are easily duplicated and can approximate the continuous type of liquid and gas exposure that occurs in wells and flow lines in the oil field. One test simulating field usage has achieved some following in the industry. The continuous exposure procedure set forth in the January 1968 issue of "Material Protections" at pages 34–35 was followed to test the subject invention. The test offers an excellent indication of the ability of corrosion inhibitors to protect metals immersed in either sweet or sour fluids.

A second test was generally followed for evaluating scale inhibition against gypsum or calcium sulfate deposition. The test is described in detail in "Corrosion", Vol. 17 (5), pp 232t–236t (1961) with modifications described below.

The following examples will further illustrate the novel scale and corrosion treating solutions of the present invention containing said phosphonate/amine reaction products. These examples are given by way of illustration and not as limitations on the scope of the invention. Thus, it should be understood that materials present in the corrosion treating solutions may be varied to achieve similar results within the scope of the invention.

EXAMPLES

General Test Procedure

The metal specimens were immersed in sweet or sour fluid environments for seventy-two (72) hours to approximate continuous exposure conditions in the oil field. The sweet fluid test environment was established by gassing the test solution with carbon dioxide. A sour fluid test environment was created by bubbling hydrogen sulfide through the test solution. The specimens were tested in both carbon dioxide and hydrogen sulfide environments with and without the claimed amines.

The metal test specimens were cold-rolled, mild steel coupons which measured 3 inches by 0.5 inches by 0.005 inches. These coupons were initially cleaned in order to remove any surface film, dried and then weighed.

Four ounce glass bottles were filled with two types of test solutions. The first simulated an oil-brine environment and consisted of 10 milliliters of Texaco EDM fluid, a Texaco trademarked lube oil cut having an API gravity of about 39°, 90 milliliters of a 10% synthetic brine and 1 milliliter of dilute (6%) acetic acid. The synthetic brine contained 10% sodium chloride and 0.5% calcium chloride by weight. The second test solution simulated a brine environment and was composed of 100 milliliters of the same 10% synthetic brine and 1 milliliter of dilute acetic acid. The oil-brine and brine test solutions were then gassed for 5 to 10 minutes with carbon dioxide to create a sweet test environment or hydrogen sulfide to create a sour test environment. The solution gassing was designed to remove any dissolved oxygen as well as create the sweet or sour environment. Next, a measured concentration of the phosphonate/amine reaction product was placed in the bottles.

The steel test coupons were then placed within the bottles. The bottles were capped and mounted on the spokes of a 23 inch diameter, vertically mounted wheel and rotated for 72 hours at 30 rpm inside an oven maintained at 49° C. The coupons were removed from the bottles, washed and scrubbed with dilute acid for cleaning purposes, dried and weighed. The corrosion rate in mils per year (mpy) was then calculated from the weight loss. One mpy is equivalent to 0.001 inches of metal lost per year to corrosion. Additionally, the test coupons were visually inspected for the type of corrosive attack, e.g., hydrogen blistering, pitting and crevice corrosion or general corrosion.

The laboratory tests for calcium sulfate scaling were performed with the testing apparatus of the Corrosion article mentioned above, the disclosure of which is incorporated herein by reference. The procedure discussed in the Corrosion article was loosely followed, with some differences as noted below. The apparatus deposits scale on heated stainless steel rotors that turn in water solutions of the scale forming minerals of calcium sulfate. Cylindrical electric heaters were mounted in the shafts to fit inside the rotor tubes which are slip fitted onto the shafts. A chain and pulley arrangement drove the rotor shafts from the variable speed motor. Line voltage for the variable speed motor was controlled by a variable transformer and a rheostat was employed to control the heaters.

In preparation for the tests, the rotors were cleaned with steel wool, rinsed with deionized water and acetone, and dried. Just prior to use, the rotors were filmed with a dilute stearic acid solution (1000 ppm in toluene) and dried. Beakers containing the scaling solutions were placed in position to submerge the rotors. The surface of the scaling solution was covered with mineral oil to prevent evaporation. Rotation of the rotors at 40 rpm was commenced and the test conducted at about 105° F. for 10–16 hours.

Two separate stock solutions were prepared and mixed to yield the final scaling test solution. One solution (Solution A) contained 468 g NaCl, 121.5 g $CaCl_2.2H_2O$, and 9722 ml of deionized water. The second solution (Solution B) contained 130.05 g of anhydrous $Na_2SO_4$ diluted to one liter with deionized water.

Each beaker in a scaling test contained 440 ml of Solution A, 40 ml of Solution B and sufficient inhibitor diluted into 20 ml of deionized water to yield the desired test concentration. Utilizing these amounts yielded test solutions which contained 50,000 ppm NaCl and 10,000 ppm $CaSO_4$. For example, to obtain a 10 ppm inhibitor concentration, 5 ml of 1000 ppm inhibitor stock solution and 15 ml of deionized water would be added to the test beaker.

Upon completion of the tests, the rotors were removed from the test apparatus, rinsed with acetone, and dried. The scale adhering to the rotors was scraped off the rotor surface and then weighed. Percent inhibition was determined by comparing the amount of deposition in uninhibited solutions (blanks) to the amount in inhibited solutions. A standard value of 1.5 g $CaSO_4$ was used for the blank.

EXAMPLE 1-6

Two phosphonates were reacted with an alkoxylated amine in the following examples. Monsanto Dequest 2060 is a phosphonate (diethylenetriaminepentamethylene phosphonic acid) with five phosphonate groups having the formula

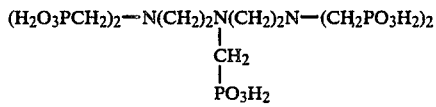

Olin NTP-A is a phosphonate having the formula

The amine reacted with the phosphonates was an amine of the disclosed formula wherein R was an alkyl group having nine carbon atoms, x was about 9.5 and z was about 3. In Examples 2 and 4, the amine reacted comprised 83.3% of the instant amine and 16.7% ethanolamine. The phosphonate/amine reaction products were prepared by heating the reactants to about 150° F. prior to the addition of the solvent.

Examples 1-6 were tested in the sweet and sour environment at 12.4 ppm under two different fluid conditions, an oil/brine fluid and a brine fluid composed as described above. Percentage reduction and corrosion ca be calculated by subtracting the results of Examples 1-4 from the corrosion rates without any corrosion inhibiting solution, which are given in Examples 5 and 6, dividing the difference by the blank value, and multiplying by 100. The sour corrosion protection was outstanding with these inhibitors.

TABLE I

| Ex. | Inhibitor | Sweet ($CO_2$) Tests | | Sour ($H_2S$) Tests | |
|---|---|---|---|---|---|
| | | oil/brine | brine | oil/brine | brine |
| 1. | Monsanto Dequest 2060 Plus Amine In A 1/1 Ratio | 9.36 | 3.64 | 1.96 | 3.28 |
| 2. | Dequest 2060 Reacted With 83.3% Amine And 16.7% Ethanolamine | 10.84 | 3.76 | 3.28 | 3.76 |
| 3. | Olin NTP-A plus Amine In A 1/1 Ratio | 10.64 | 3.04 | 5.32 | 3.76 |
| 4. | Olin NTP-A Reacted With 83.3% Amine And 16.7% Ethanolamine | 5.92 | 4.60 | 2.64 | 2.88 |
| 5. | None | 12.2 | 13.6 | — | — |
| 6. | None | — | — | 50.8 | 55.2 |

EXAMPLE 7-9

The scaling test described at the beginning of the examples was followed in the laboratory to produce the results of Table II at different concentrations.

TABLE II

| | | CaSO₄ Scale Inhibition Tests | | | | | | | |
|---|---|---|---|---|---|---|---|---|---|
| | Ex. | % CaSO₄ Inhibition For Inhibitor Concentrations | | | | | | | |
| Ex. | No. Inhibitor | 0.5 ppm | 1.25 ppm | 1.75 ppm | 2.5 ppm | 3.75 ppm | 5.0 ppm | 7.5 ppm | 10 ppm |
| 7 | 1 | 6 | 22 | 11 | 14 | 30 | 46 | — | — |
| 8 | 2 | 0 | 11 | 40 | 46 | 50 | 83 | 99 | 100 |
| 9 | 4 | 0 | 10 | 15 | 12 | 4 | 33 | — | — |

The combination of the amine whose formula was disclosed above wherein R was an alkyl group having nine carbon atoms, x was about 9.5 and z was about 3 and the Dequest 2060 organic phosphonate produced superior calcium sulfate (gypsum) scale control at low concentrations. Ninety-nine percent protection against calcium sulfate scale was achieved at only 7.5 ppm concentration of inhibitor in Example 8. Although the compound was only tested for calcium sulfate scale inhibition, it is believed to be also effective against calcium carbonate scale. Compounds that are this effective against calcium sulfate scale are almost always effective in carbonate scale control.

Other variations and modifications may be made in the concepts described above by those skilled in the art without departing from the concepts of the present invention. Accordingly, it should be clearly understood that the concepts disclosed in the description are illustrative only and are not intended as limitations on the scope of the invention.

What is claimed is:

1. A water-dispersible corrosion and scale inhibiting solution comprising:
   a solvent; and
   about 2 ppm to about 1% by volume of the reaction product of a phosphonate compound having at least two phosphonate groups of the formula

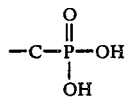

with an ethoxylated, propoxylated alkylphenol amine represented by the formula

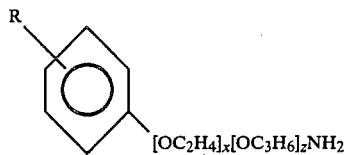

wherein R is an alkyl group containing about 5 to about 12 carbon atoms, x equals about 1 to about 20, and z equals about 1 to about 20.

2. The corrosion and scale inhibiting solution of claim 1, wherein the solvent is water.

3. The corrosion and scale inhibiting solution of claim 2, wherein the solvent is brine.

4. The corrosion and scale inhibiting solution of claim 1, wherein the solvent is a hydrocarbon and brine mixture.

5. The corrosion and scale inhibiting solution of claim 1, wherein R is an alkyl group containing about 7 to about 10 carbon atoms, x equals about 4 to about 11, and z equals about 2 to about 5.

6. The corrosion and scale inhibiting solution of claim 1, wherein the concentration of said phosphonate/amine reaction product is about 3 ppm to about 200 ppm.

7. The corrosion and scale inhibiting solution of claim 1, wherein the phosphonate and amine are reacted in the proportions of about 0.9/1 phosphonate/amine ratio to about 1/0.9 phosphonate/amine ratio.

8. The corrosion and scale inhibiting solution of claim 1, wherein the phosphonate has the formula

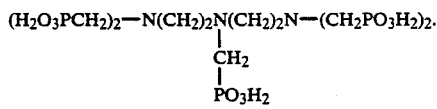

9. The corrosion and scale inhibiting solution of claim 1, wherein the phosphonate has the formula

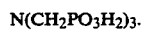

10. A water-dispersible corrosion and scale inhibiting solution comprising:
   water; and
   about 3 ppm to about 200 ppm by volume of the reaction product of a phosphonate compound having about two to about six phosphonate groups of the formula

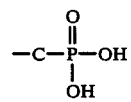

with an ethoxylated, propoxylated alkylphenol amine represented by the formula

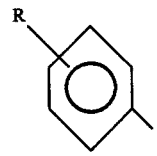

wherein R is an alkyl group containing about 7 to about 10 carbon atoms, x equals about 4 to about 11, and z equals about 2 to about 5, said phosphonate and amine reacted in the proportions of about 0.9/1 phosphonate/amine to about 1/0.9 phosphonate/amine.

11. A water-dispersible corrosion and scale inhibiting solution comprising:
   about 0% to about 99% by volume of water;
   about 0% to about 99% by volume of an alcohol; and
   about 1% to about 70% by volume of the reaction product of a phosphonate compound having about two to about six phosphonate groups of the formula

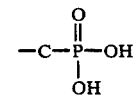

with an ethoxylated, propoxylated alkylphenol amine, said amine represented by the formula

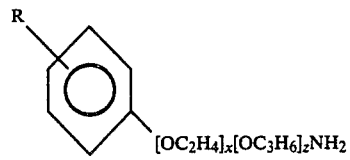

wherein R is an alkyl group containing about 5 to about 12 carbon atoms, x equals about 1 to about 20, and z equals about 1 to about 20.

12. The corrosion and scale inhibiting solution of claim 11, wherein water comprises about 30% to about 80% by volume of the solution, alcohol comprises about 5% to about 40% by volume of the solution, and said phosphonate/amine reaction product comprises about 15% to about 60% by volume of the solution.

13. The corrosion and scale inhibiting solution of claim 11, wherein R as an alkyl group containing about 7 to about 10 carbon atoms, x equals about 4 to about 11 and z equals about 2 to about 5.

14. The corrosion and scale inhibiting solution of claim 11, wherein the alcohol is selected from the group of alcohols consisting of methanol, ethanol, propanol, isopropanol, butanol, pentanol, ethylene glycol, propylene glycol, and mixtures thereof.

15. The corrosion and scale inhibiting solution of claim 11, wherein the alcohol is a mixture of methanol and ethylene glycol.

16. A method of protecting metals from scale and corrosive agents in hydrocarbon and aqueous fluids which comprises contacting metal with an effective amount of the reaction product of a phosphonate compound having at least two phosphonate groups of the formula

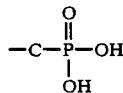

with an amine compound represented by the formula

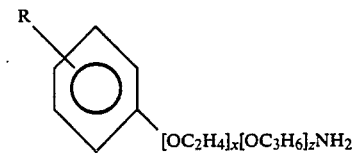

wherein R is an alkyl group containing about 5 to about 12 atoms, x equals about 1 to about 20, and z equals about 1 to about 20.

17. The method of claim 16, wherein said phosphonate/amine reaction product is mixed with fluid so that a concentration of about 3 ppm to about 200 ppm of said reaction produce continuously contacts the metal.

* * * * *

UNITED STATES PATENT AND TRADEMARK OFFICE
CERTIFICATE OF CORRECTION

PATENT NO. : 4,950,474

DATED : August 21, 1990

INVENTOR(S) : Charles J. Hinrichsen and Frederick W. Valone

It is certified that error appears in the above-identified patent and that said Letters Patent is hereby corrected as shown below:

In Claim 16, at Col. 10, line 53, please insert

--carbon-- before "atoms".

Signed and Sealed this

Tenth Day of March, 1992

*Attest:*

HARRY F. MANBECK, JR.

*Attesting Officer*     *Commissioner of Patents and Trademarks*